(12) United States Patent
Agarwal et al.

(10) Patent No.: US 10,478,239 B2
(45) Date of Patent: Nov. 19, 2019

(54) PEDICLE SCREW ASSEMBLY

(71) Applicants: Anand K. Agarwal, Holland, OH (US); Aakash Agarwal, Toledo, OH (US)

(72) Inventors: Anand K. Agarwal, Holland, OH (US); Aakash Agarwal, Toledo, OH (US)

(73) Assignee: Spinal Balance, Inc., Holland, OH (US)

( * ) Notice: Subject to any disclaimer, the term of this patent is extended or adjusted under 35 U.S.C. 154(b) by 149 days.

(21) Appl. No.: 14/773,575

(22) PCT Filed: Mar. 10, 2014

(86) PCT No.: PCT/US2014/022685
§ 371 (c)(1),
(2) Date: Sep. 8, 2015

(87) PCT Pub. No.: WO2014/138736
PCT Pub. Date: Sep. 12, 2014

(65) Prior Publication Data
US 2016/0022341 A1 Jan. 28, 2016

Related U.S. Application Data

(60) Provisional application No. 61/775,080, filed on Mar. 8, 2013.

(51) Int. Cl.
*A61B 17/86* (2006.01)
*A61B 17/70* (2006.01)
*A61B 90/00* (2016.01)

(52) U.S. Cl.
CPC ...... *A61B 17/8685* (2013.01); *A61B 17/7032* (2013.01); *A61B 17/7037* (2013.01); *A61B 17/8605* (2013.01); *A61B 2090/037* (2016.02)

(58) Field of Classification Search
CPC ............ A61B 17/8685; A61B 17/7032; A61B 17/7037
USPC .................. 606/273–275, 305–308
See application file for complete search history.

(56) References Cited

U.S. PATENT DOCUMENTS

| | | | | |
|---|---|---|---|---|
| 5,217,497 A | * | 6/1993 | Mehdian | A61B 17/1671 606/268 |
| 5,443,467 A | * | 8/1995 | Biedermann | A61B 17/7032 606/308 |
| 5,964,760 A | * | 10/1999 | Richelsoph | A61B 17/7037 606/278 |
| 6,077,262 A | * | 6/2000 | Schlapfer | A61B 17/7032 606/264 |

(Continued)

FOREIGN PATENT DOCUMENTS

WO 2010017631 A1 2/2010

OTHER PUBLICATIONS

European Extended Search Report, Application No. EP 14760535.6, dated Oct. 21, 2016.

*Primary Examiner* — Matthew J Lawson
(74) *Attorney, Agent, or Firm* — MacMillan, Sobanski & Todd, LLC (57) ABSTRACT

A pedicle screw assembly includes a threaded shank portion formed from a polymer material and a head assembly. The head assembly includes a tulip having extending arms, the tulip engaging a reaction bar such that loads applied to the pedicle screw assembly can be transferred to another pedicle screw assembly in order to immobilize a section of a spinal column.

6 Claims, 11 Drawing Sheets

(56) References Cited

U.S. PATENT DOCUMENTS

| | | | |
|---|---|---|---|
| 6,641,586 B2 * | 11/2003 | Varieur | A61B 17/7032 411/403 |
| 7,951,173 B2 | 5/2011 | Hammill, Sr. et al. | |
| 8,100,947 B2 | 1/2012 | Ensign et al. | |
| 8,137,384 B2 | 3/2012 | Heiges et al. | |
| 2002/0143341 A1 * | 10/2002 | Biedermann | A61B 17/7032 606/308 |
| 2003/0023243 A1 * | 1/2003 | Biedermann | A61B 17/7032 606/308 |
| 2003/0100904 A1 * | 5/2003 | Biedermann | A61B 17/7032 606/272 |
| 2003/0125741 A1 * | 7/2003 | Biedermann | A61B 17/7032 606/278 |
| 2006/0161153 A1 * | 7/2006 | Hawkes | A61B 17/7032 606/278 |
| 2008/0195159 A1 | 8/2008 | Kloss et al. | |
| 2009/0062868 A1 | 3/2009 | Casutt | |
| 2009/0292308 A1 * | 11/2009 | Jones | A61B 17/7032 606/205 |
| 2010/0228293 A1 | 9/2010 | Courtney et al. | |
| 2010/0228300 A1 | 9/2010 | Armstrong et al. | |
| 2010/0241170 A1 * | 9/2010 | Cammisa | A61B 17/7032 606/264 |
| 2012/0203286 A1 * | 8/2012 | Armstrong | A61B 17/8685 606/304 |
| 2013/0023941 A1 * | 1/2013 | Jackson | A61B 17/7005 606/305 |
| 2013/0085536 A1 * | 4/2013 | Biedermann | A61B 17/7076 606/308 |
| 2013/0103096 A1 * | 4/2013 | Miller | A61B 17/7032 606/305 |

* cited by examiner

PEDICLE SCREW ASSEMBLY

CROSS-REFERENCE TO RELATED APPLICATIONS

This application claims the benefit of U.S. Provisional Application No. 61/775,080, filed Mar. 8, 2013, the disclosure of which is incorporated herein by reference.

BACKGROUND OF THE INVENTION

This invention relates in general to orthopedic surgical implants and, more specifically, to a polymer- or hybrid-based metal/polymer pedicle screw fixation system for use in the field of surgical spine treatment.

Surgical techniques for the treatment of spinal injuries or deformities are usually aimed at joining together two or more vertebrae of the spine, through a process that is called spinal fusion. A spinal fusion technique relies on a fixation system that is anchored to the spine by way of orthopedic screws. These screws are implanted into the pedicles of two or more subsequent vertebrae. The screws implanted into each pedicle are connected together by means of rigid or semi-rigid rods. These rods engage a transverse hole provided in the screw heads, for example, as shown in FIG. 1.

Spinal fixation can be used to treat scoliosis, spondylolisthesis, degenerative disc disease, vertebra fracture, and other spinal disorders or abnormalities. These screws provide rigidity to spinal segments by mechanically immobilizing them. Spinal fixation devices are also used to correct abnormal curvature of the spine.

Pedicles connect the vertebral body to the posterior elements. Each vertebra has two pedicles. Pedicle screws include a threaded shaft and slots at the screw head. The threaded shafts are screwed into the spine through the respective pedicles and a rod locks the screws in place to minimize relative motion, often resulting in a loosening of the screws. The rods are typically locked into place with a fastening screw or set screw.

Current pedicle screws are made out of metal, typically, stainless steel or titanium. These metal screws are very rigid. This high level of rigidity has shown to cause screw loosening in elderly patients or patients with soft bone, as in the case of osteoporosis, multiple myeloma or tumor. These problems include screw loosening, adjacent level degeneration and facet joint degeneration.

There is a continuing need for a pedicle screw fixation system that militates against screw loosening in use. Desirably, the pedicle screw fixation system also militates against adjacent level degeneration and facet joint degeneration.

SUMMARY OF THE INVENTION

This invention relates to a pedicle screw assembly for use in immobilizing a section of a spinal column. The pedicle screw assembly includes a head assembly having a tulip. A threaded shank portion is formed from a polymer material and is connected to the tulip. In one embodiment, the polymer material is a PEEK polymer material.

In another aspect of the invention, a pedicle screw assembly includes a head assembly having a tulip, where the tulip includes a base and extending arms. The extending arms include at least one threaded surface, and the base has a pocket configured to receive a reaction bar. A fastener engages the at least one threaded surface to secure the reaction bar against the pocket. A threaded shank portion, formed from a polymer material, has a controlled compliance that reduces a localized yielding of a bone material away from the threaded shank portion caused by loads applied to the reaction bar. The threaded shank portion of the pedicle screw assembly has a screw thread that engages the bone material. The threaded shank portion has a deflection characteristic that is similar to that of the surrounding bone material such that stresses are reduced at the screw thread/bone interface region.

In yet another aspect of the invention, a pedicle screw fixation system includes a first pedicle screw assembly and a second pedicle screw assembly. The first pedicle screw assembly includes a tulip having a pocket configured to receive a reaction bar and a threaded shank portion formed from a polymer material. The second pedicle screw assembly includes a tulip having a pocket configured to receive a reaction bar and a threaded shank portion formed from a polymer material. The fixation system also includes a reaction bar that interconnects the first and second pedicle screw assemblies together such that a load applied to the first pedicle screw assembly is transferred to the second pedicle screw assembly. The polymer threaded shank portions are formed from a polymer having a hardness that prevents localized yielding of the bone material away from the threaded shank portions.

Various aspects of this invention will become apparent to those skilled in the art from the following detailed description of the preferred embodiments, when read in light of the accompanying drawings.

DETAILED DESCRIPTION OF THE PREFERRED EMBODIMENT

Figure 1A:
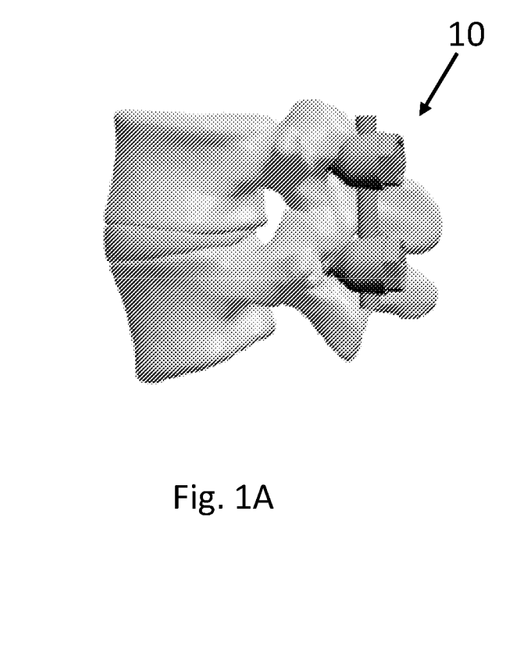
FIG. 1A is a perspective view of a pedicle screw fixation system installed in a pair of adjoining vertebrae.
Figure 1B:
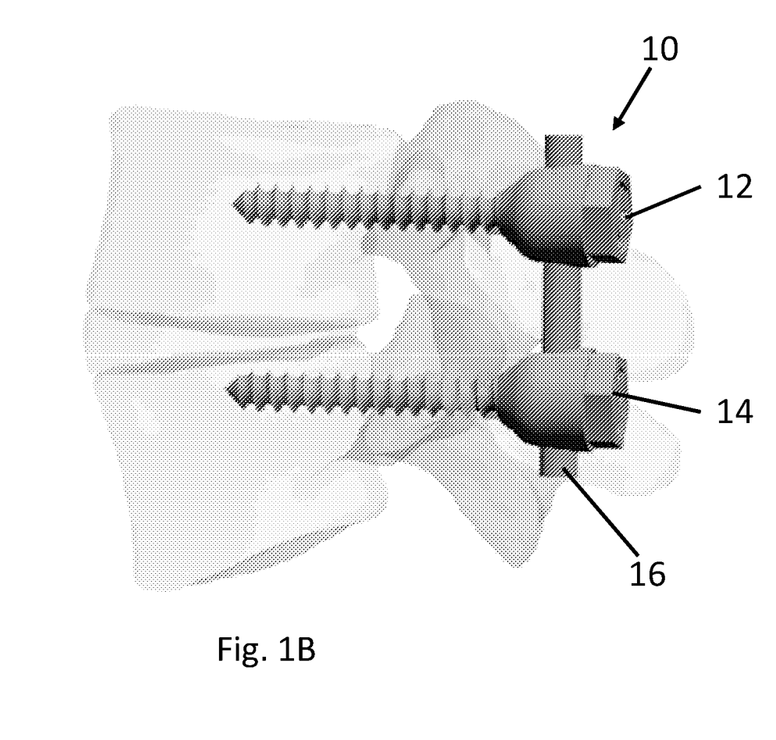
FIG. 1B is an enlarged perspective view of the installed pedicle screw fixation system of FIG. 1A.

Referring now to the drawings, there is illustrated in FIGS. 1A and 1B a pedicle screw fixation system, indicated generally at 10 that is installed in a pair of adjoining vertebrae. The pedicle screw fixation system 10 includes a first pedicle screw assembly 12 and a second pedicle screw assembly 14 connected together by a fixation bar or reaction bar 16. The pedicle screw assemblies 12 and 14 are illustrated as being identical in configuration and construction, though such is not required. Each of the pedicle screw assemblies 12 and 14 is configured to be inserted into a vertebra, such as the illustrated adjacent vertebrae, in order to immobilize sections of a spine. In certain procedures, immobilizing the spinal sections is for fusion of the vertebrae. Each of the pedicle screw assemblies 12, 14 is screwed into holes drilled into portions of the vertebrae. Once the pedicle screw assemblies 12, 14 are in position, the reaction bar 16 interconnects the two pedicle screw assemblies 12, 14 to prevent relative movement of the pedicle screw assemblies 12, 14. The reaction bar 16 may be held in place by set screws or other retaining features. Though illustrated as having a round, generally cylindrical shape, the reaction bar 16 may have any shape, such as square, rectangular, hexagonal, oval, and the like. Portions of the pedicle screw assembly 12 are formed from a polymer material such as polyesteresterketone (PEEK), a thermoplastic polymer in the polyaryletherketone (PAEK) family. Alternatively, portions of the pedicle screw assembly 12 may be formed from a reinforced polymer material, such as a particulate reinforced plastic or a fiber reinforced plastic.

As observed by the inventor, the broad disparity in rigidity of prior art metal pedicle screws compared with the surrounding bone material, especially in patients having soft or weakened bone structure, results in loosening of the screws and degradation of bone over time. The loosening of the screw assemblies is hastened by the rigid screws working against the softer bone material, causing localized displacement and compression of the bone. This localized displacement around the screw threads permits the structure to rock and wallow-out or otherwise enlarge the drilled holes, causing movement and bone structure degradation. The use of polymer materials for portions of the pedicle screw assembly 12, in accordance with the invention, has resulted in preventing, or greatly reducing, loosening and the degradation of surrounding bone material. While not wishing to be bound by theory, the inventor believes that the controlled compliance of the overall structure is closer to that of the surrounding bone material, thus reducing stress concentrations at the screw thread/bone interface region. This more gradual transition of deflections, and thus stress states, from screw to bone prevents localized yielding of the bone material away from the screw threads. The reduction of sharp stress discontinuities at the interface of the screws, along with improvements in coefficient of friction between the bone material and the screw, prevents the pedicle screw assemblies 12, 14 from loosening.

Figure 2A:
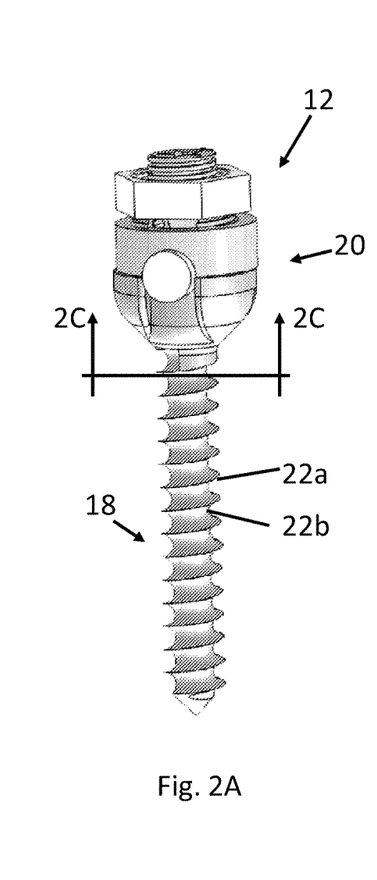
FIG. 2A is a perspective view of a first embodiment of a pedicle screw assembly for use in a pedicle screw fixation system.
Figure 2B:
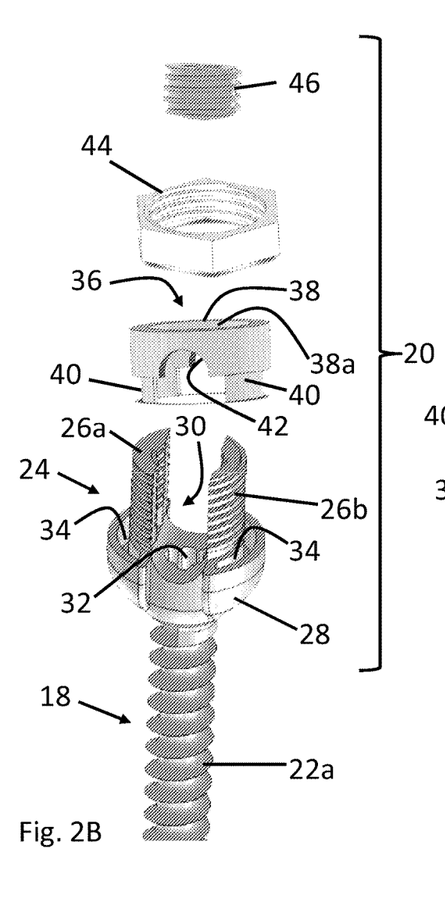
FIG. 2B is an exploded view of the pedicle screw assembly of FIG. 2A.
Figure 2C:
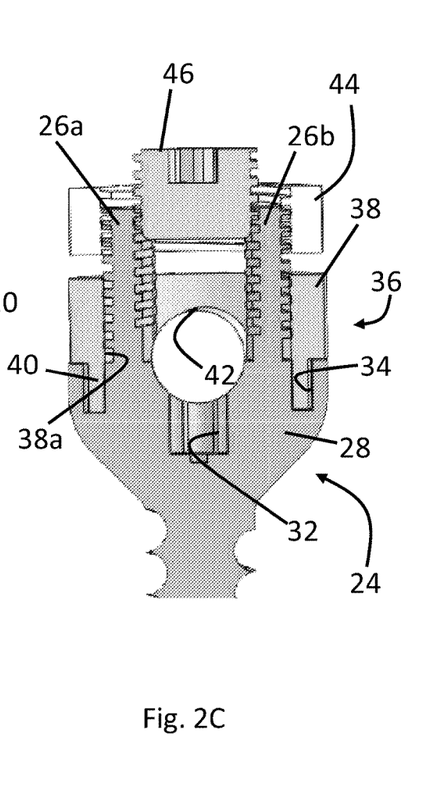
FIG. 2C is a cross-sectional view of a head portion of the pedicle screw assembly of FIG. 2A taken along line 2C-2C.

Referring now to FIGS. 2A-2C, there is illustrated in detail the first embodiment of the pedicle screw assembly, shown generally at 12. The pedicle screw assembly 12 includes a threaded shank portion 18 and a head assembly 20. The threaded shank portion 18 may have any configuration of thread form desired. In the illustrated embodiment, the thread form consists of spaced-apart, auger shaped spiraling thread elements 22a having a radius or fillet 22b connecting adjacent auger forms. Other thread forms, however, may be used and are considered to be within the scope of this disclosure. The thread form may be a cutting tread form, where a portion of the spiral thread 22a cuts or imbeds itself into the bone material as it is screwed into the hole drilled into the bone. Alternatively, the thread form may partially imbed in the bone and partially deform within the hole creating a combined frictional and thread-locked fit. In yet another alternative arrangement, the thread form may be completely deformed within the hole to maintain position by friction.

The head assembly 20 includes an anchoring U-clamp or tulip, shown generally at 24. In the illustrated embodiment, the threaded shank portion 18 and the tulip 24 are formed from a polymer material. In one aspect of the illustrated embodiment, the shank and tulip 18 and 24 are integrally formed from PEEK. The integrally formed tulip 24 and threaded shank portion 18 form a mono-axial structure having a single centerline. The tulip 24 is configured to have a pair of extending arms 26a and 26b that are threaded on both an outer diameter surface and an inner diameter surface. The extending arms 26a and 26b extend from a base 28 and are spaced-apart to define a central opening 30 that accepts the reaction bar 16. The base 28 includes a drive aperture 32, located between the extending arms 26a and 26b, that has a torque transmitting profile. The drive aperture 32 is configured to permit a driver, such as a screw driver, to rotate the threaded shank portion 18 into the bone material. The torque transmitting profile may be any suitable geometry, such as a slot, cross, hexagonal shape, Torx®; or any other profile that permits the threaded shank portion 18 to be rotated into the bone material. The base 28 further includes a pair of pilot slots 34 that extend around each of the extending arms 26a and 26b.

A clamping cap 36 includes an outer bridge ring 38 that defines an opening 38a configured to permit the extending arms 26a and 26b to extend therethrough. In one embodiment, the clamping cap 36 may be made from a polymer, such as PEEK. Alternatively, the clamping cap 36 may be made from a metal, such as stainless steel or titanium. The opening 38a of the bridge ring 38 provides radial and transverse support to the extending arms 26a and 26b in response to loads applied by the reaction bar 16 during use. The clamping cap 36 further includes a pair of extending pilot tabs 40 that are configured to engage the pilot slots 34 when assembled onto the tulip 24. A mating bar retaining profile 42 is formed into the outer bridge ring 38 that aids in trapping and retaining the reaction bar 16 in the tulip 24. The retaining profile 42 may be generally the same shape as the reaction bar 16, or may have a mating feature with the reaction bar 16, such as mating flat profiles, to prevent movement of the reaction bar 16 and locate its position relative to the tulip 24. A retaining nut 44 threads onto the outer threads of the extending arms 26a and 26b to secure the clamping cap 36 against the tulip 24 and the reaction bar 16. A set screw 46 is configured to engage the inner threads of the extending arms 26a and 26b. The set screw 46 may be configured to abut and press against the reaction bar 16 to frictionally retain the reaction bar 16 within the tulip 24. The set screw 46 may additionally be configured to outwardly deflect the extending arms 26a and 26b against the retaining nut 44 such that the retaining nut 44 is frictionally prevented from rotating loose. The retaining nut 44 and set screw 46 may be made from a polymer material or a metal, if desired.

Figure 3A:
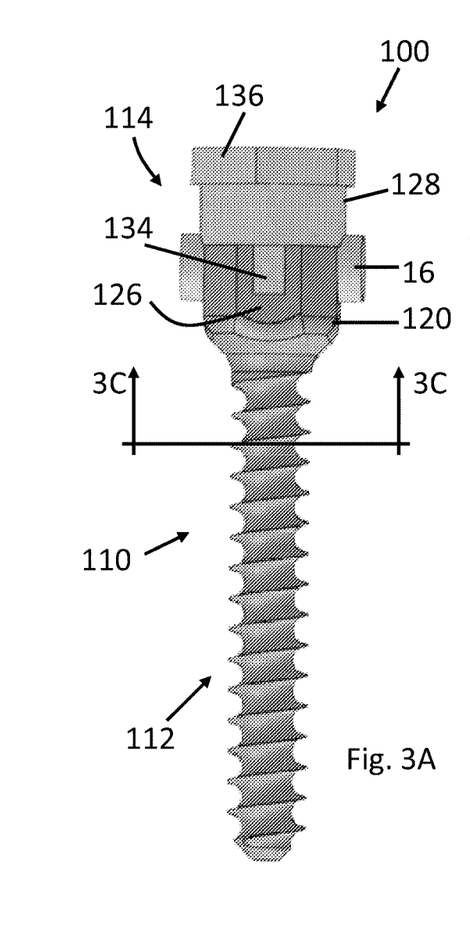
FIG. 3A is a perspective view of a second embodiment of a pedicle screw assembly for use in a pedicle screw fixation system.
Figure 3B:
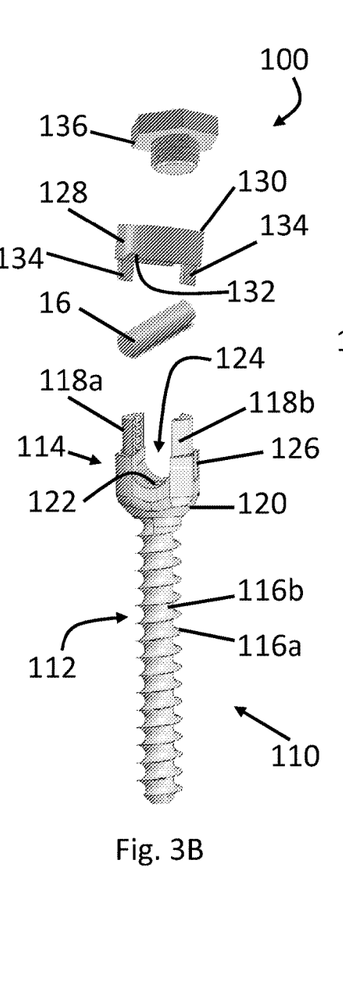
FIG. 3B is an exploded view of the pedicle screw assembly of FIG. 3A.
Figure 3C:
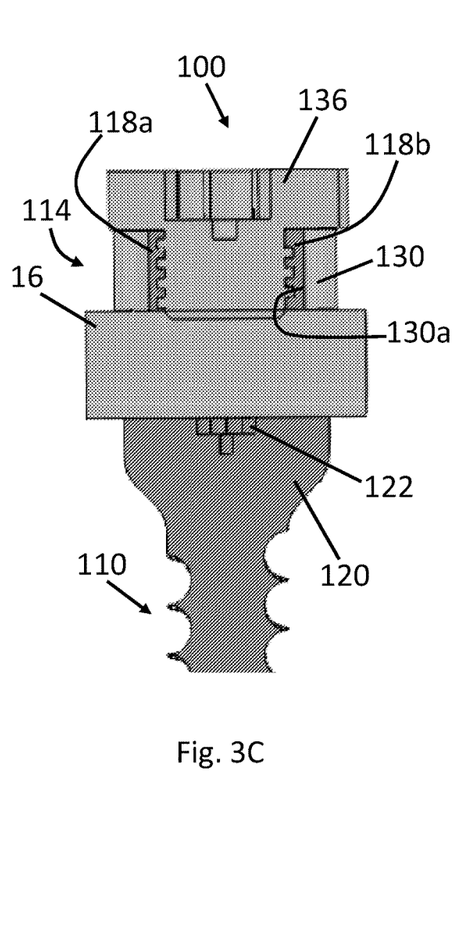
FIG. 3C is a cross-sectional view of a head portion of the pedicle screw assembly of FIG. 3A taken along line 3C-3C.

Referring now to FIGS. 3A-3C, there is illustrated a second embodiment of a pedicle screw assembly, shown generally at 100. Similar to the pedicle screw assembly 12, the second embodiment pedicle screw assembly 100 includes a pedicle screw 110 having a threaded shank portion 112 and a tulip 114. The pedicle screw 110 is made from a polymer, such as PEEK. The threaded shank portion 112 includes an auger-type spiral tooth form 116a and a fillet 116b between adjacent tooth profiles. As previously disclosed, other tooth forms may be used if desired. The tulip 114 includes extending arms 118a and 118b that are threaded on an inner diameter surface. The outer surface of the extending arms 118a and 118b is generally smooth. The extending arms 118a and 118b are integrally connected to a base 120 that is also integrally formed with the threaded shank portion 112 to form a mono-axial pedicle screw 110. The base 120 includes a drive aperture 122, similar to drive aperture 32, described above. The base 120 is U-shaped to define a pocket 124 that retains the reaction bar 16 within the tulip 114. The base 120 has a thickened section in the area defining the pocket 124, as compared to the pedicle screw assembly 12 above. This thickened section provides additional strength and rigidity to securely hold and retain the reaction bar 16. The base 120 includes locating surfaces 126 generally in line with and offset from the extending arms 118a and 118b.

A clamping cap 128 is similarly configured to clamping cap 36. The clamping cap 128 may be made from a polymer, such as PEEK or a fiber reinforced plastic, or from a metal, such as titanium or stainless steel. The clamping cap 128 includes an outer bridge ring 130 that defines an opening 130a that permits the extending arms 118a and 118b to extend therethrough. Thus, the bridge ring 130 provides rigidity and stability to the tulip 114. The clamping cap 128 further includes a retaining profile 132 that traps and secures the reaction bar 16 between the cap and the pocket 124. The clamping cap 128 further includes alignment tabs 134 that extend from the bridge ring 130 and locate against the locating surfaces 126 of the base 120. A flanged retaining bolt 136 is configured to engage the inner surface threads of the extending arms 118a, 118b and draw the clamping cap 128 onto the reaction bar 16. The end of the bolt 136 may contact the reaction bar 16, as shown in FIG. 3C, to further secure the assembly together.

Referring now to FIGS. 4A-4D, there is illustrated a pedicle screw assembly, shown generally at 200. The pedicle screw assembly 200 includes a pedicle screw 210 and a tulip 212. The tulip 212 is configured to be pivoted or angled relative to the pedicle screw 210. The pedicle screw 210 includes a threaded shank portion 214 that terminates in a pivot head 216. The pivot head 216 has a generally rounded shape having a diameter that is larger than the major diameter of the threaded shank portion 214. Thus, the pivot head 216 extends outwardly, away from the screw centerline, further than the remainder of the threaded shank portion 214. The pivot head 216 further includes a drive aperture 218.

The tulip 212 includes a base 220 having spaced-apart extending arms 222. The extending arms 222 include a threaded inner surface. The base 220 defines a U-shaped pocket 224 and a pivot aperture 226 opposite the extending arms 222. The pivot aperture 226 is sized such that the threaded shank portion 214 of the pedicle screw 210 will pass through, but the pivot head 216 is retained within the base 220. The pivot head 216 is free to pivot relative to the base 220 prior to tightening the assembly 200 in an installed condition with the reaction bar 16. A pivot saddle 228 includes a socket aperture 230 that has a complementary shape to the generally spherical shape of the pivot head 216. The outer diameter 232 of the pivot saddle 228 fits inside the upper portion of the pivot aperture 226 such that a saddle 234 of the pivot saddle 228 aligns with the U-shaped pocket 224 of the base 220 and locates against the reaction rod 16. The pedicle screw 210 and the pivot saddle 228 are inserted into the tulip 212 between the extending arms 222 such that the threaded shank portion 214 extends through the pivot aperture 226.

Figures 4A, 4B, 4D:
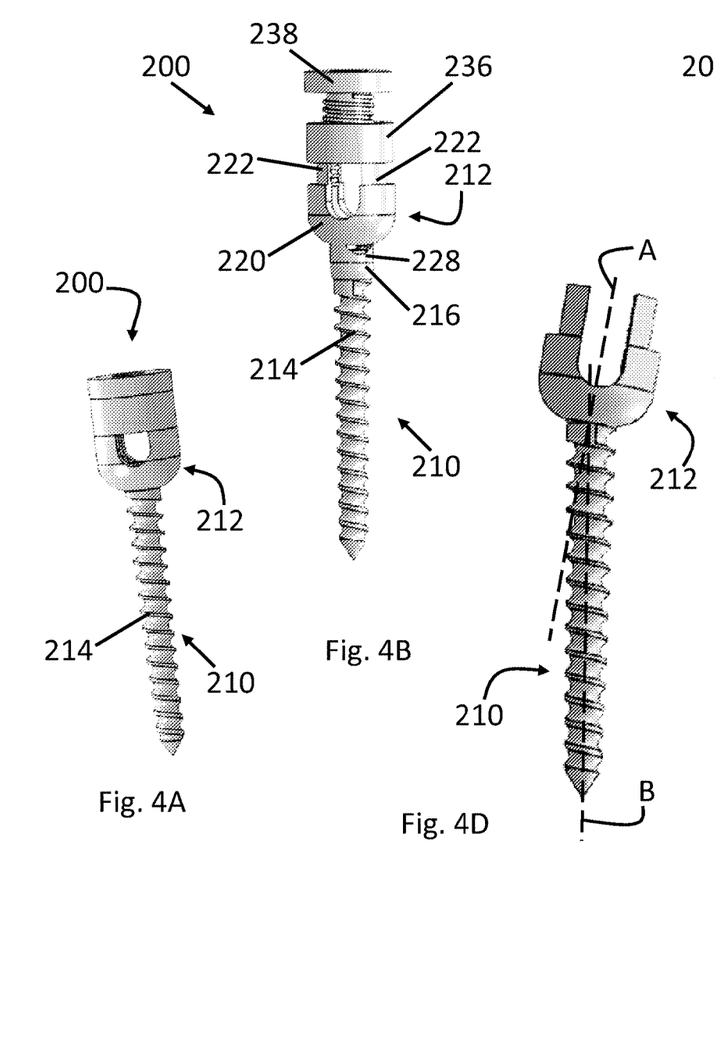
FIG. 4A is a perspective view of a third embodiment of a pedicle screw assembly.
FIG. 4B is an exploded, perspective view of the pedicle screw of FIG. 4A.
FIG. 4D is a side view of the pedicle screw of FIG. 4A and related axes.
Figure 4C:
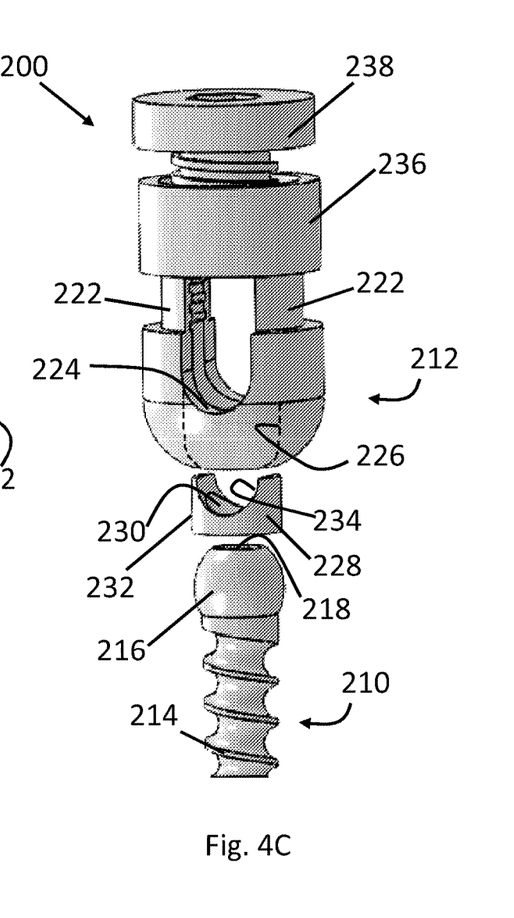
FIG. 4C is an enlarged, exploded view of the pedicle screw of FIG. 4A.

A clamping cap 236 is configured as a cylindrical sleeve having an outer and an inner diameter. The inner diameter slides over the outer surface of the extending arms 222 and both secures the reaction bar 16 in place and provides rigidity to the extending arms 222. A flanged retaining bolt 238 threads into engagement with the threaded inner surface of the extending arms 222. The flange of the bolt 238 engages the clamping cap 236 and creates a frictional engagement with the reaction bar 16 to secure it in place. In addition, the flange bolt 238 also secures and fixes the tulip 212 relative to the pivot head 216 of the pedicle screw 210. As can be seen in FIG. 4D, the axis A of the tulip 212 can be angled relative to the axis B of the pedicle screw 210. The ability to rotate and angle the tulip 212 relative to the pedicle screw 210 permits two opposing U-shaped pockets 224 to be aligned to accept the reaction bar 16. This alignment of the tulips 212 can be achieved without requiring a high degree of parallelism between the adjacent pedicle screw axes B.

Figures 5A, 5B:
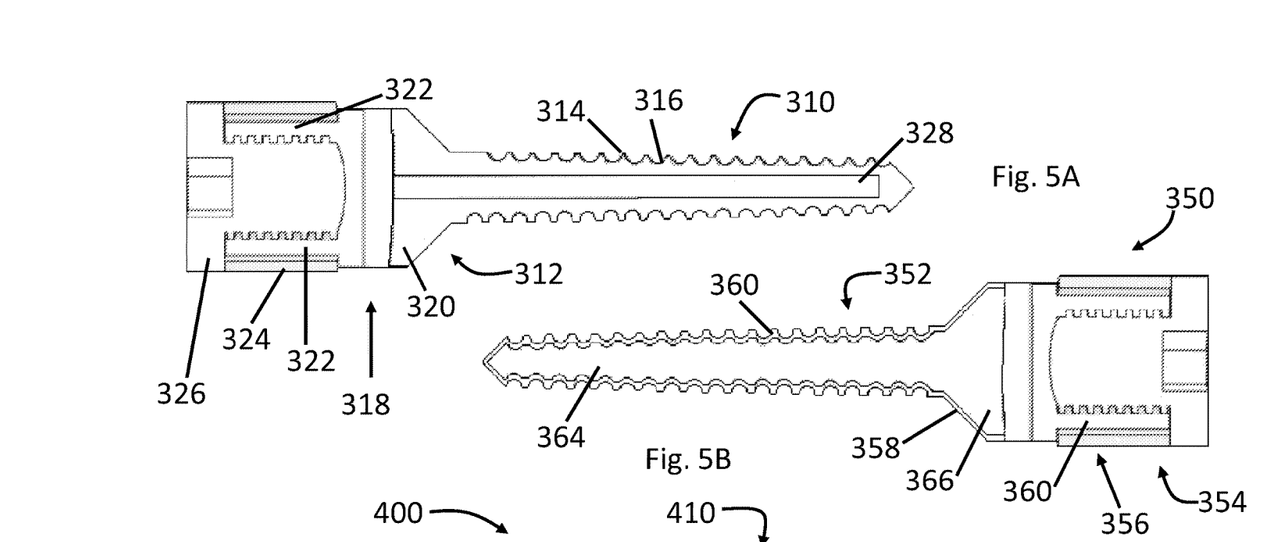
FIG. 5A is a cross-sectional view of a fourth embodiment of a pedicle screw assembly.
FIG. 5B is a cross-sectional view of an alternative configuration of the pedicle screw assembly of FIG. 5A.

Referring now to FIG. 5A, there is illustrated a fourth embodiment of a pedicle screw assembly, shown generally at 300. The pedicle screw assembly 300 is similar to the embodiments described above, particularly the embodiment of FIGS. 3A-3C, and includes a threaded shank portion 310 and a head assembly 312. The threaded shank portion 310 includes an auger-type spiral tooth form 314 and a fillet 316 between adjacent tooth profiles. As previously disclosed, other tooth forms may be used if desired. The head assembly 312 includes a tulip 318 that is integrally formed with the threaded shank portion 310. In the illustrated embodiment, the threaded shank portion 310 and the tulip 318 are integrally formed as a single mono-axial structure and made from a polymer, such as PEEK. The tulip 318 includes a base 320 and threaded arms 322 that extend from the base 320 away from the threaded shank portion 310. The extending arms 322 are threaded on an inner diameter surface, and the outer surface is generally smooth. The head assembly 312 further includes a clamping cap 324 and a retaining flange bolt 326, similar to the clamping cap 128 and flanged bolt 136 described above. The base 320 may include a drive aperture (not shown), similar to drive aperture 32, described above.

The integrally formed tulip 312 and threaded shank portion 310 includes a reinforcing wire 328. The reinforcing wire 328 is molded in the general center of the polymer threaded shank portion 310 and extends from near the tip end into the base 320. The reinforcing wire 328 may be a metal material, a higher Young's Modulus polymer material (higher than PEEK) or may be a fiber reinforced plastic. The reinforcing wire 328 provides an increased bending stiffness of the overall assembly, while the polymer threaded shank portion 310 engages the bone material. Thus, the bending stiffness of the pedicle screw assembly 300 is increased, but the deflection characteristics of the screw/bone interface are more closely matched. This prevents the threads from enlarging the hole formed into the bone.

Referring now to FIG. 5B, there is illustrated a variation of the inner reinforced pedicle screw assembly 300. A reinforced pedicle screw assembly, shown generally at 350 includes a threaded shank portion 352 and a head assembly 354. A tulip 356, having a base 358 and extending arms 360, is formed integrally with the threaded shank portion 352. The threaded shank portion 352 and the base 358 are reinforced with an outer shell 360. The outer shell 362 may be a metal shell, such as a titanium or stainless steel shell, having a generally thin wall compared to the overall cross section of the threaded shank portion 352. In one embodiment, the outer shell may be in a range of about 5% to about 20% of the average thickness of a polymer core 364 of the threaded shank portion 352. The base 358 is further characterized by a polymer core 366. The polymer cores 364 and 366 may be a single polymer material and, in one embodiment, may be a PEEK polymer core. The thickness of the shell 362 is sufficiently thin so that the structural stiffness of the base 358 and the threaded shank portion is similar to or within a +/−30% range of the bending stiffness of the PEEK formed threaded shank portion 18 of FIGS. 2A-2C. In addition, the shell 362 permits the polymer cores 364 and 366 to be made from a softer material than PEEK. The outer shell 362 is also ductile and flexible, thus reducing the deflection discontinuities at the screw/bone interface compared with a solid metal pedicle screw.

Figures 6A, 6B, 6C:
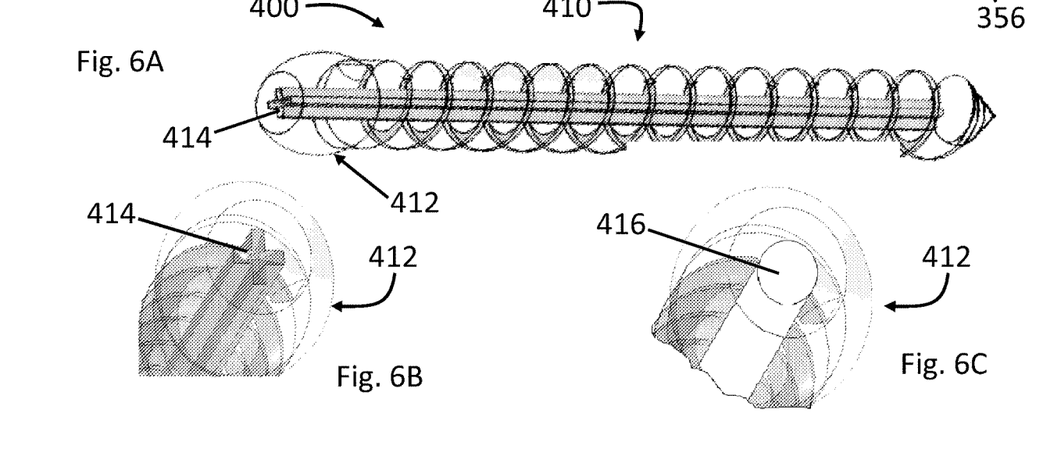
FIG. 6A is a perspective view of a fifth embodiment of a pedicle screw having a reinforcement, a portion of the screw shown in phantom.
FIG. 6B is an enlarged perspective view of a head portion of the pedicle screw of FIG. 5A.
FIG. 6C is an enlarged perspective view of a head portion of a sixth embodiment of a pedicle screw having a reinforcement, similar to the pedicle screw of FIGS. 5A and 5B.

Referring now to FIGS. 6A-6C, there is illustrated a fifth embodiment of a poly-axial pedicle screw, shown generally at 400. The poly-axial pedicle screw 400 may be used in conjunction with components from any of the poly-axial embodiments described herein, such as the embodiment shown in FIGS. 4A-4D and described above. The poly-axial pedicle screw 400 includes a threaded shank portion 410 and a pivot head 412. The pedicle screw 400 is formed from a polymer material, such as PEEK or a similar plastic-based material having similar properties. A reinforcing wire 414 is molded in the general center of the pedicle screw 400. The reinforcing wire 414 is illustrated as having a "cross" or "phillips head" cross-sectional geometry, as shown in FIG. 6B. Other geometries may be used, such as a square, hexagonal, star, or other radially symmetric shape. A round reinforcing wire 416 is shown in FIG. 6C. The reinforcing wire 414 provides an increased bending stiffness, yet the molded polymer exterior alleviates the otherwise greater hardness discontinuity at the screw thread/bone interface.

Figure 7A:
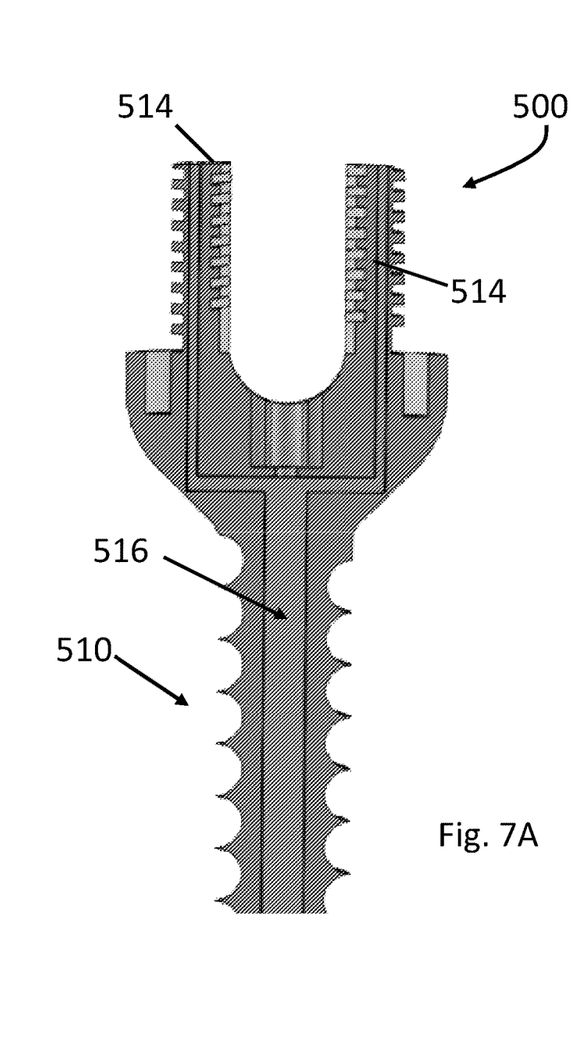
FIG. 7A is a cross-sectional view of a seventh embodiment of a pedicle screw having a reinforcement.
Figure 7B:
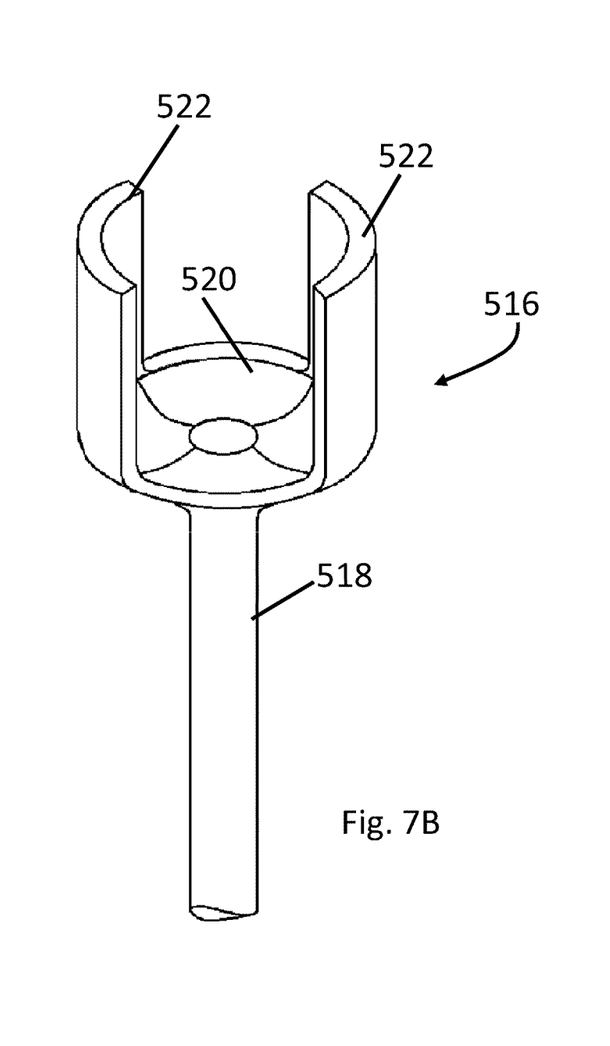
FIG. 7B is a perspective view of the reinforcement of FIG. 7A.

Referring now to FIGS. 7A and 7B, there is illustrated a mono-axial pedicle screw, shown generally at 500. The mono-axial pedicle screw 500 includes a polymer threaded shank portion 510 and an integrally formed polymer tulip 512 having extending threaded arms 514. Embedded within the polymer threaded shank portion 510 and the tulip 512 is a reinforcement 516. The reinforcement 516 is a single structure that includes a shank reinforcement 518, a base reinforcement 520 and extending arm reinforcements 522. In the illustrated embodiment, the reinforcement 516 is completely contained within the polymer shank 510 and tulip 512. Alternatively, the reinforcement 516 may have a portion, such as the extending arm reinforcements 522 that may protrude from the polymer encapsulation. In such a configuration, the extending arms 522 may have inner and/or outer threads formed thereon. The reinforcement 516 provides rigidity to the shank portion 510 and the tulip 512, particularly for applications that require additional loading profiles, such as growth rods and their manipulating structures (not shown).

Figure 8:
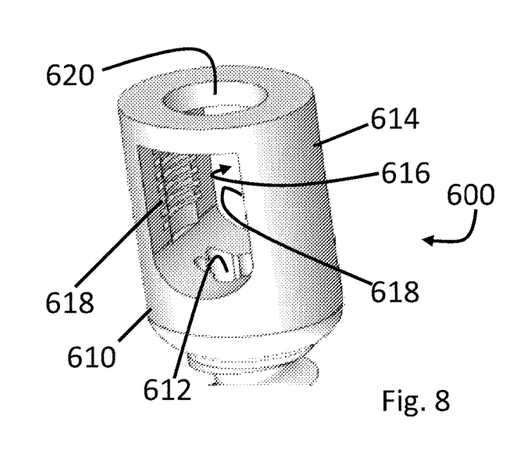
FIG. 8 is a perspective view of an eighth embodiment of a head portion of a pedicle screw.
Figure 9:
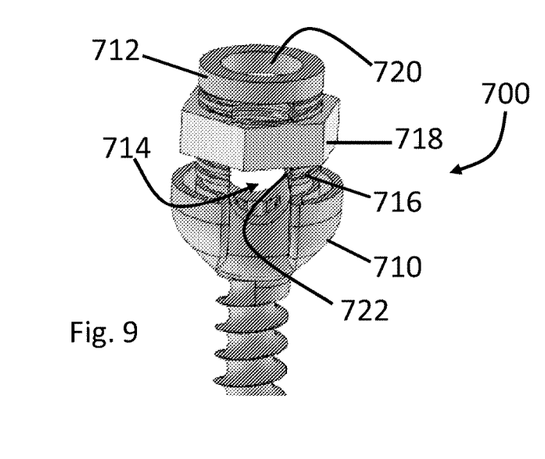
FIG. 9 is a perspective view of a ninth embodiment of a pedicle screw assembly.

Referring now to FIGS. 8, 9, 10A and 10B, there are illustrated several embodiments of pedicle screws having various polymer tulip configurations having a closed upper section. As shown in FIG. 8, a tulip 600 includes a base 610 having a drive aperture 612. The tulip 600 is illustrated as having a mono-axial construction with the threaded shank portion, as described above. A generally cylindrical wall section 614 extends from the base 610 having a reaction bar aperture 616 formed therethrough. The wall section 614 includes opposed inner surfaces 618 having threads formed thereon. A set screw aperture 620 permits a set screw to engage the threads and secure the reaction bar 16 in place. FIG. 9 illustrates another embodiment of a mono-axial polymer-formed, closed tulip, shown generally at 700. The polymer closed tulip 700 includes an integral base 710, that is similar to base 28, described above. A generally cylindrical wall section 712 extends from the base 710 and includes a reaction bar aperture 714 formed therethrough. The generally cylindrical wall section 712 includes an outer surface 716 having threads formed thereon to engage a retaining nut 718. The wall section 712 includes a set screw aperture 720 and an inner surface 722 having threads to accept a set screw (not shown). Alternatively, the inner surface may be generally smooth.

Figures 10A, 10B:
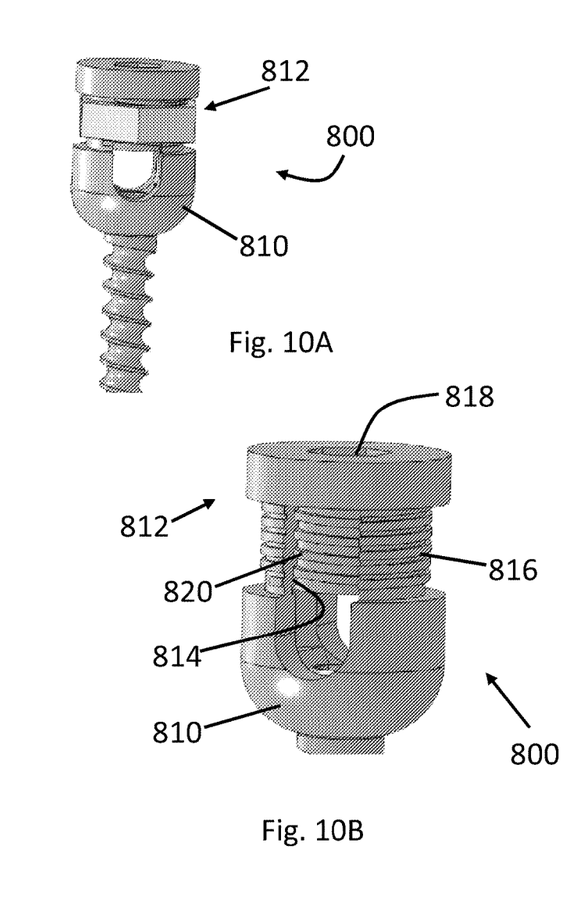
FIG. 10A is a perspective view of a tenth embodiment of a pedicle screw assembly.
FIG. 10B is a perspective view of a portion of the pedicle screw assembly of FIG. 10A.

Referring now to FIGS. 10A and 10B, there is illustrated an embodiment of a closed tulip, shown generally at 800, that is configured as a poly-axial tulip. The closed tulip 800 may be similarly configured for adjustable, pivotal movement similar to the embodiment shown in FIGS. 4A-4D, though such a specific arrangement is not required. The closed tulip 800 may be formed from a polymer or a metal. The closed tulip 800 includes a base 810 and a generally cylindrical wall section 812 extending from the base 810. The cylindrical wall section 812 includes threaded inner and outer surfaces 814 and 816, respectively. The wall section 812 includes a set screw aperture 818 configured to permit a set screw 820 to engage the reaction bar. The threads of the outer surface 816 are configured to permit a retaining nut to engage a clamping cap (not shown).

Figure 11A:
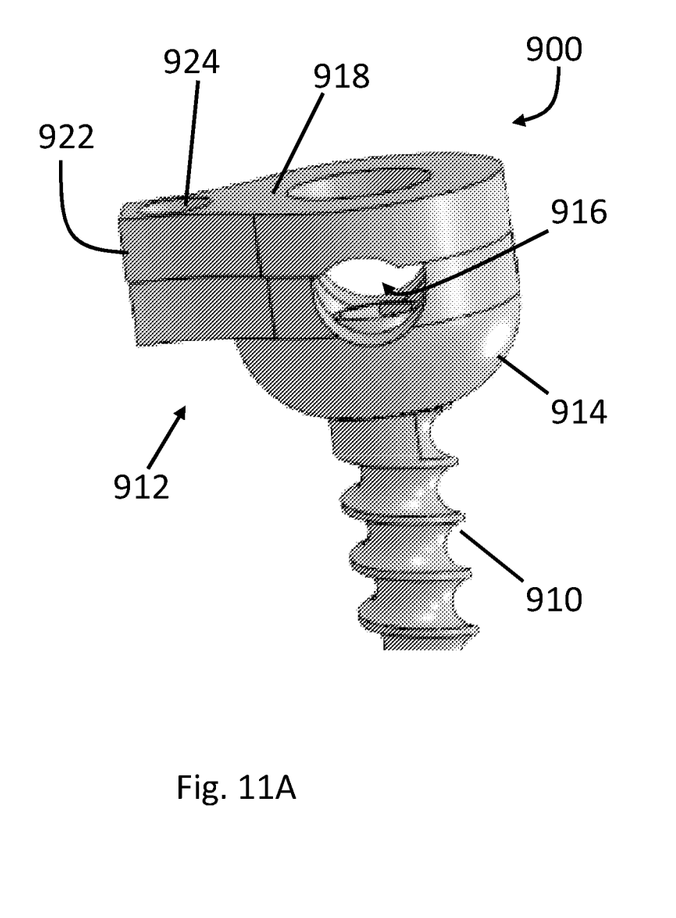
FIG. 11A is a perspective view of a head portion of an eleventh embodiment of a pedicle screw assembly in a closed position.
Figure 11B:
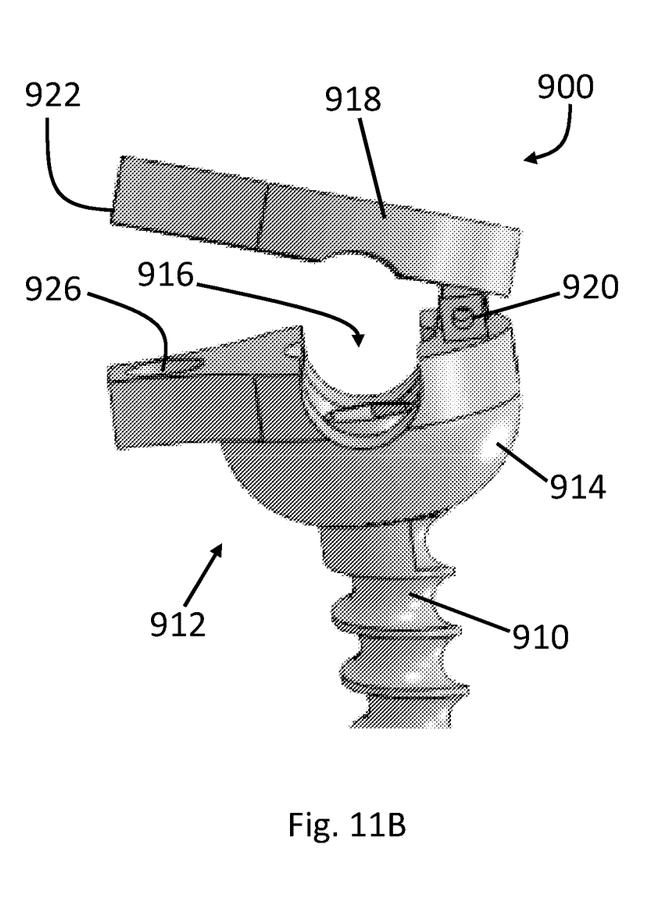
FIG. 11B is a perspective view of the head portion of the pedicle screw assembly of FIG. 11A in an opened position.
Figure 12:
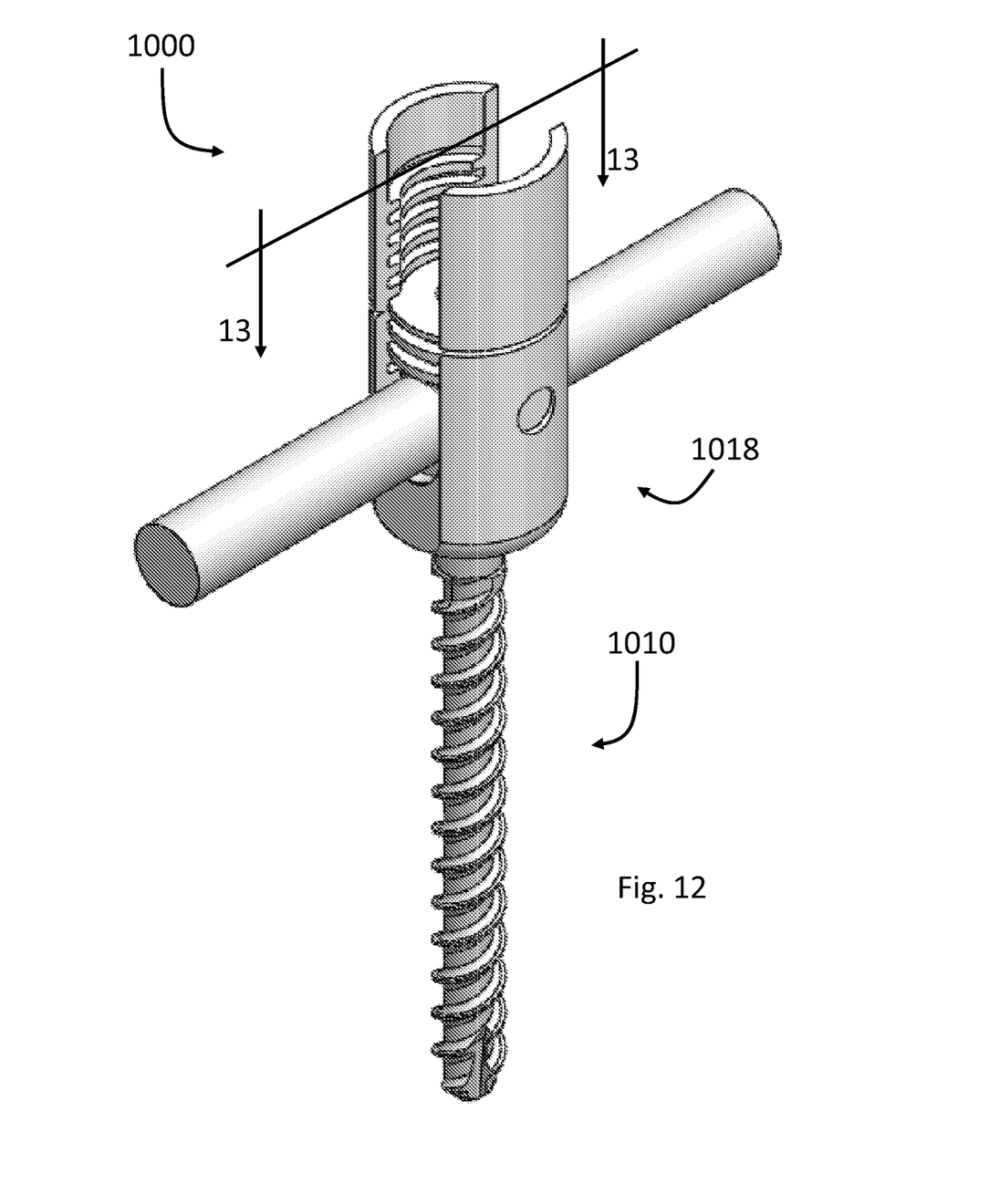
FIG. 12 is a perspective view of a twelfth embodiment of a pedicle screw assembly.

Referring now to FIGS. 11A and 11B, there is illustrated an embodiment of a pedicle screw assembly, shown generally at 900. The pedicle screw assembly is illustrated as a poly-axial pedicle screw assembly, similar to the poly-axial pedicle screw assembly 200 though such is not required. Alternatively, the pedicle screw assembly 900 may be configured as a mono-axial assembly. The pedicle screw assembly 900 includes a threaded shank portion 910, configured similarly to the threaded shank portion 210 of FIGS. 4A-4D. A tulip assembly 912 is pivotally mounted on the threaded shank portion 910. The tulip assembly 912 includes a base 914 having a U-shaped saddle 916 formed therethrough. The tulip assembly 912 includes a hinged cover 918 having a hinged end 920 and a closure end 922. The hinged end 920 permits the cover to be moved from a closed position, as shown in FIG. 11A, to an open position, as shown in FIG. 11B. The closure end 922 includes a closure aperture 924 that may be a through hole and a locking aperture 926 that may be a threaded aperture such that a bolt (not shown) may fasten the hinged cover 918 in the closed position.

Figures 13A, 13B:
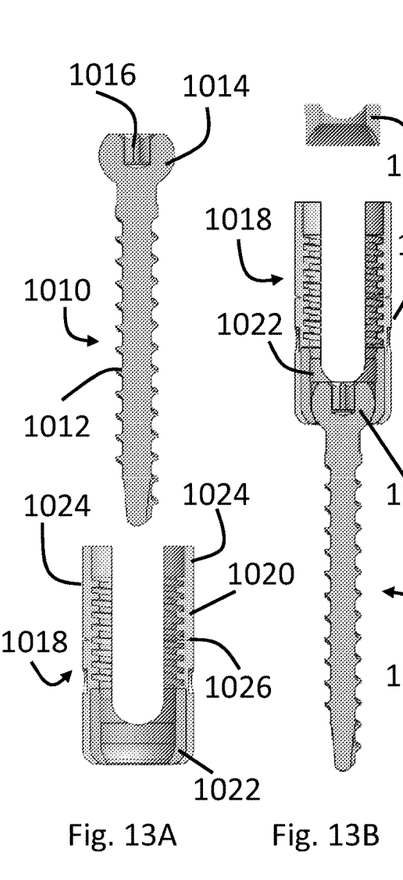
FIGS. 13A-13F are cross-sectional, exploded views of an assembly sequence of the pedicle screw assembly of FIG. 12, taken along line 13-13.
Figures 13C, 13D:
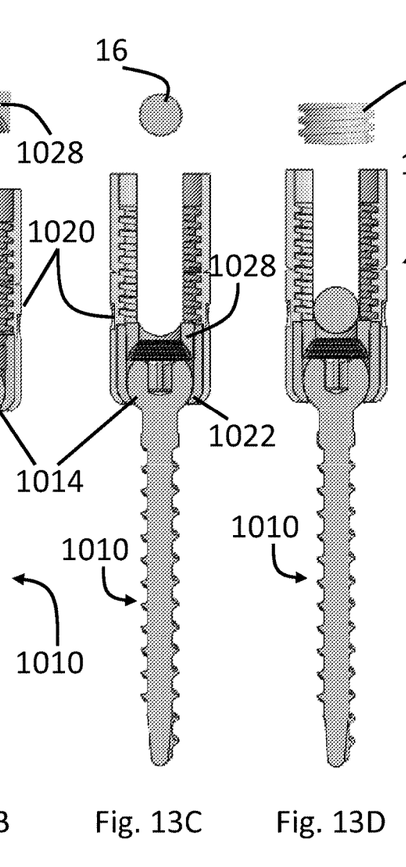
Figure 13E:
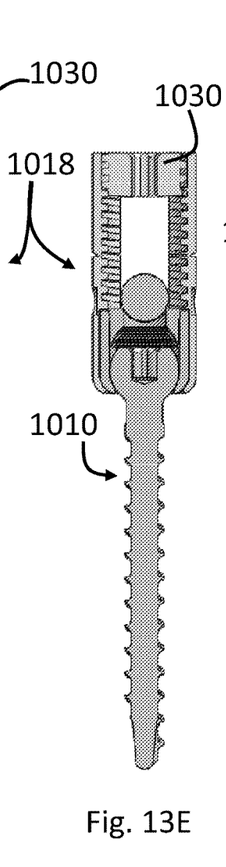
Figure 13F:
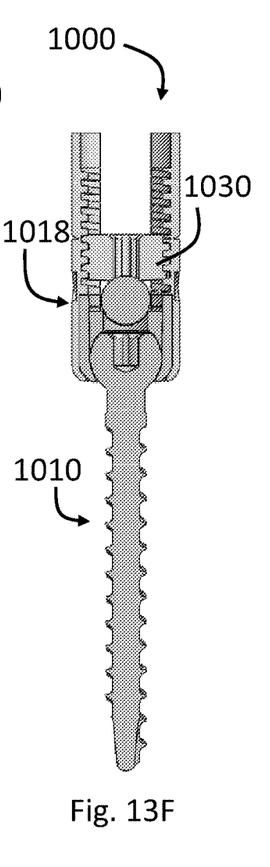

Referring now to FIGS. 12 and 13A-13F, there is illustrated a poly-axial pedicle screw assembly, shown generally at 1000. The pedicle screw assembly 1000 includes a pedicle screw 1010 having a threaded shank portion 1012 and a pivot head portion 1014 that includes a drive aperture 1016. The pedicle screw 1010 may be similar in configuration to the pedicle screw 210 or the reinforce pedicle screw 400, described above. A tulip assembly 1018 includes a tulip housing 1020, that may be formed from metal, and a pivot bushing 1022, that is formed from a polymer. The tulip housing includes a pair of extending arms 1024 having threaded inner surfaces. The extending arms 1024 include a frangible section 1026 that permits the extending arms to be reduced in height. The pedicle screw 1010 is inserted into an open end of the tulip housing 1020 and extends through the tulip assembly 1018 until the pivot head 1014 seats in the pivot bushing 1022, as shown in FIG. 13B. The pivot bushing 1022 supports the pivot head 1014 for relative movement. A pivot saddle 1028 is inserted through the open end of the tulip housing 1020 and locates against the upper portion of the pivot head 1014, as shown in FIG. 13C. The reaction bar 16 is inserted between the extending arms 1024 and seats against the upper portion of the pivot saddle 1028 as shown in FIG. 13D. A set screw 1030 is threaded between the extending arms 1024 and tightened against the reaction bar 16 to secure it in place, as shown in FIGS. 13E-13F.

Figure 14:
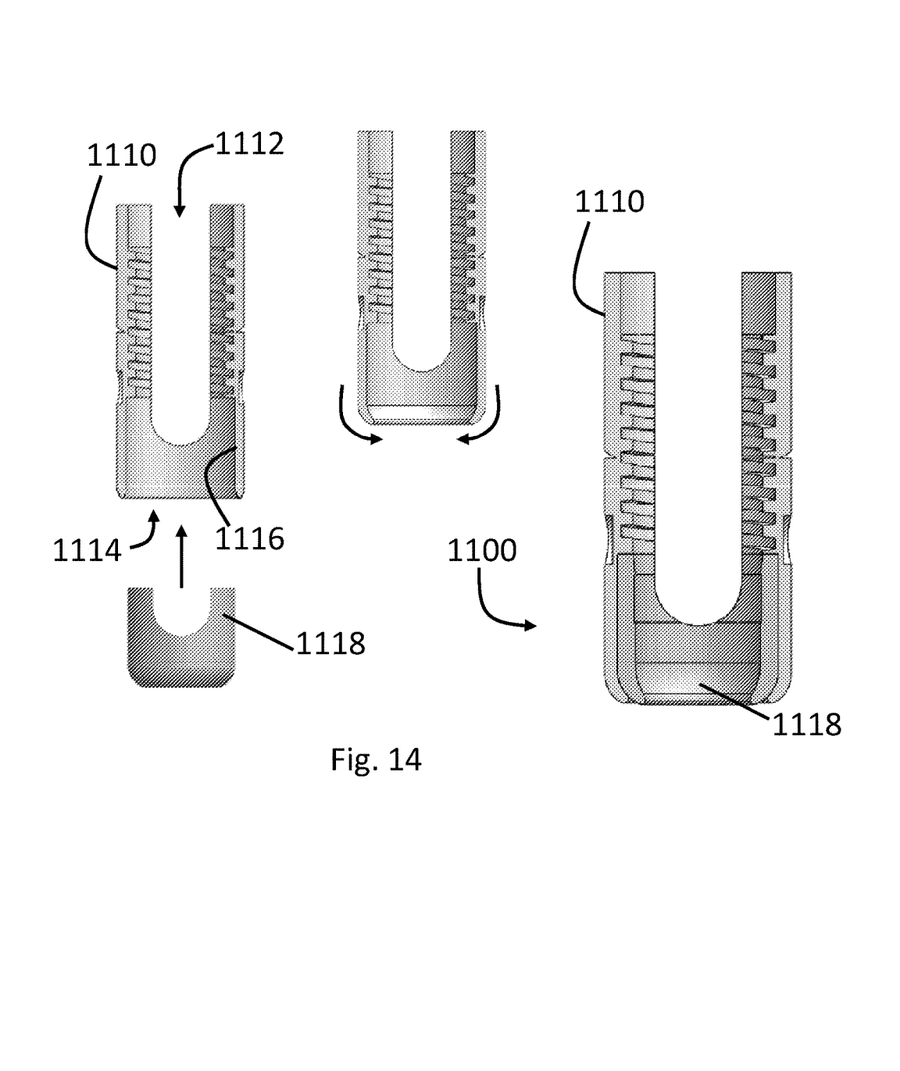
FIG. 14 is an embodiment of a method of forming a portion of the pedicle screw assembly of FIG. 12.

Referring now to FIG. 14, there is illustrated an embodiment of a hybrid tulip assembly, shown generally at 1100, that is similar to the tulip assembly 1018, above. The hybrid tulip assembly 1100 includes a tulip housing 1110 having a bar open end 1112 and a pivot end 1114. The pivot end 1114 includes a counterbore 1116 that is configured to accept a pivot bushing 1118. As shown in FIG. 14, the pivot bushing is inserted into the counterbore 1116. After the pivot bushing 1118 is seated in the counterbore 116, the pivot end 1114 is upset or otherwise closed over the pivot bushing 1118 to restrain and fix the bushing in the housing.

Figure 15:
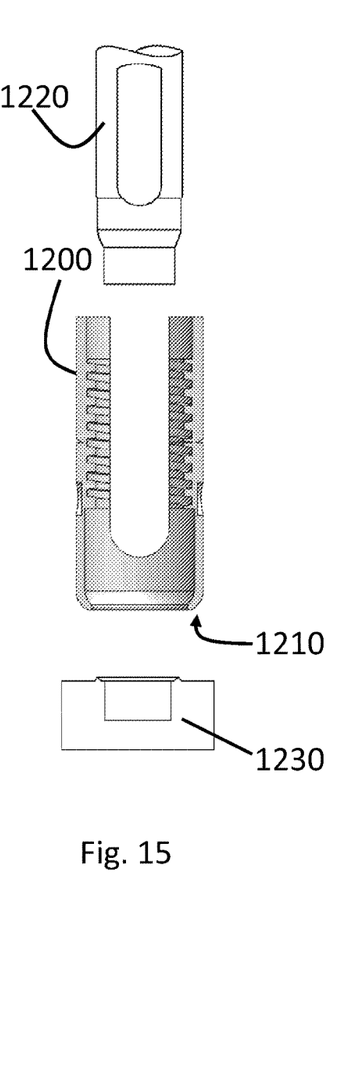
FIG. 15 is another embodiment of a method of forming a portion of the pedicle screw assembly of FIG. 12.

Referring to FIG. 15, an alternative assembly method may include a tulip housing 1200 having a pivot end 1210 that is configured to have a reduced opening sufficient to permit a pedicle screw, such as pedicle screw 1010, to extend through but retain the pivot bushing and pivot head within the housing 1200. An inner mold 1220 and an end mold 1230 may be brought together relative to the housing 1200 to form a cavity having the shape of the pivot bushing 1118. The pivot bushing 1118 may be then molded, such as by injection molding into the housing 1200.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A pedicle screw assembly comprising:
 a head assembly including a tulip having a U-shaped pocket defined by a pair of extending arms, each of the extending arms including a threaded inner surface and a threaded outer surface;
 a threaded shank portion extending from the tulip;
 a retaining nut threadably engaged with the threaded outer surface of the extending arms; and
 a set screw threadably engaged with the threaded inner surface of the extending arms, wherein the set screw outwardly deflects the extending arms against the retaining nut such that the retaining nut is frictionally prevented from rotating.

2. The pedicle screw assembly of claim 1, wherein the tulip is integrally formed with the threaded shank portion from a single piece of a polymer material.

3. The pedicle screw assembly of claim 1, further including a clamping cap disposed about the outer threaded surface of the tulip and retaining on the tulip by the retaining nut.

4. The pedicle screw assembly of claim 3, wherein the head assembly includes a pilot slot, and wherein the clamping cap includes a pilot tab that engages the pilot slot.

5. The pedicle screw assembly of claim 1, wherein the clamping cap has a retaining profile provided therein, and wherein the retaining profile has generally the same shape as a reaction bar extending therethrough.

6. The pedicle screw assembly of claim 1, wherein the head assembly includes a drive aperture located between the extending arms.

* * * * *